(12) United States Patent
Kito et al.

(10) Patent No.: US 7,888,649 B2
(45) Date of Patent: Feb. 15, 2011

(54) RADIATION IMAGE CAPTURING SYSTEM

(75) Inventors: Eiichi Kito, Minami-ashigara (JP);
Naoyuki Nishino, Minami-ashigara (JP);
Yasunori Ohta, Yokohama (JP);
Tsuyoshi Tanabe, Odawara (JP);
Takuya Yoshimi, Yokohama (JP);
Takeshi Kuwabara, Minami-ashigara (JP); Kazuharu Ueta, Suginami-ku (JP);
Makoto Iriuchijima, Ora-gun (JP)

(73) Assignee: FUJIFILM Corporation, Tokyo (JP)

( * ) Notice: Subject to any disclaimer, the term of this patent is extended or adjusted under 35 U.S.C. 154(b) by 118 days.

(21) Appl. No.: 12/166,500

(22) Filed: Jul. 2, 2008

(65) Prior Publication Data

US 2009/0010391 A1   Jan. 8, 2009

(30) Foreign Application Priority Data

Jul. 6, 2007   (JP) .............................. 2007-178503
May 30, 2008  (JP) .............................. 2008-143214

(51) Int. Cl.
*H01L 27/146* (2006.01)

(52) U.S. Cl. .............................................. 250/370.09
(58) Field of Classification Search ................. 250/370.01–370.15; 378/97, 108, 98.8; 600/407
See application file for complete search history.

(56) References Cited

U.S. PATENT DOCUMENTS

| 4,053,774 | A | * | 10/1977 | Berdahl ........................ 378/97 |
| 6,404,851 | B1 | * | 6/2002 | Possin et al. ............... 378/98.7 |
| 7,429,737 | B2 | * | 9/2008 | Wojcik et al. .......... 250/370.09 |
| 7,573,034 | B2 | * | 8/2009 | Heath et al. .............. 250/361 R |
| 2003/0095629 | A1 | * | 5/2003 | Nascetti et al. ............ 378/98.8 |
| 2004/0114725 | A1 | * | 6/2004 | Yamamoto ................... 378/189 |

FOREIGN PATENT DOCUMENTS

| JP | 06-142089 | A | | 5/1994 |
| JP | 07-140255 | A | | 6/1995 |
| JP | 2000-105297 | A | | 4/2000 |
| JP | 2004-201757 | A | | 7/2004 |
| JP | 2007-097909 | A | | 4/2007 |
| JP | 2007121010 | | * | 5/2007 |

OTHER PUBLICATIONS

Fang et al., "Investigation of ghosting in a-Se detector under large accumulated radiation exposure," 2005, IEEE Nuclear Science Symposium Conference Record, M11-129, pp. 2483-2487.*

* cited by examiner

*Primary Examiner*—David P Porta
*Assistant Examiner*—Kiho Kim
(74) *Attorney, Agent, or Firm*—Sughrue Mion, PLLC

(57) ABSTRACT

The present invention relates to a radiation image capturing system. A radiation detector of a radiation detecting cassette detects a radiation that has passed through a patient, and an accumulated exposed radiation dose calculator calculates an accumulated exposed radiation dose by accumulating radiation image information detected by the radiation detector, at every image capturing. The calculated accumulated exposed radiation dose is transmitted, together with cassette ID information, to a console. In the console, a status determining unit compares the accumulated exposed radiation dose with an allowable accumulated exposed radiation dose for the radiation detecting cassette to determine the status of the radiation detecting cassette, and issues a warning based on the determined status.

10 Claims, 6 Drawing Sheets

RADIATION IMAGE CAPTURING SYSTEM

BACKGROUND OF THE INVENTION

1. Field of the Invention

The present invention relates to a radiation image capturing system having a radiation conversion panel for detecting a radiation that has passed through a subject and converting the detected radiation into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation, or the stimulable phosphor panel is supplied to a reading device to read the radiation image as a visible image.

In the operating room or the like, it is necessary to read and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read a detected radiation image.

Radiation image capturing systems incorporating such a radiation conversion panel manage an exposed radiation dose that is applied to a subject in order to prevent the subject from being irradiated with an excessive amount of radiation.

For example, Japanese Laid-Open Patent Publication No. 2007-097909 discloses an exposed radiation dose managing system including an image management server for calculating and accumulating an exposed radiation dose from information about radiation images of a subject and confirming the accumulated exposed radiation dose applied to the subject to prevent the subject from being irradiated with an excessive amount of radiation.

Japanese Laid-Open Patent Publication No. 6-142089 discloses an X-ray managing apparatus for determining an accumulated value representing the sum of an X-ray dose applied to a subject in the past and a predicted value of X-ray dose before the subject is irradiated with X-rays, and making an advance warning, when necessary, based on the accumulated value.

Japanese Laid-Open Patent Publication No. 2004-201757 reveals an X-ray diagnosing system which allows the accumulated exposed radiation dose of a subject to be shared by different hospital facilities.

The systems and apparatus disclosed in all the documents referred to above, manage an exposed radiation dose applied to a subject, but not a radiation dose applied to a radiation conversion panel. Since the radiation conversion panel has its sensitivity variable when irradiated with a radiation, the radiation conversion panel may fail to produce an appropriate radiation image depending on the accumulated exposed radiation dose applied thereto.

SUMMARY OF THE INVENTION

It is a general object of the present invention to provide a radiation image capturing system which is capable of producing an appropriate radiation image by managing the state of a radiation conversion panel used.

A major object of the present invention is to provide a radiation image capturing system which is capable of detecting, in advance, a change in the sensitivity of a radiation conversion panel, and issuing a warning, when necessary, based on the detected change in the sensitivity.

Another object of the present invention is to provide a radiation image capturing system which is capable of replacing and servicing a radiation conversion panel at suitable timings for producing optimum radiation images at all times.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
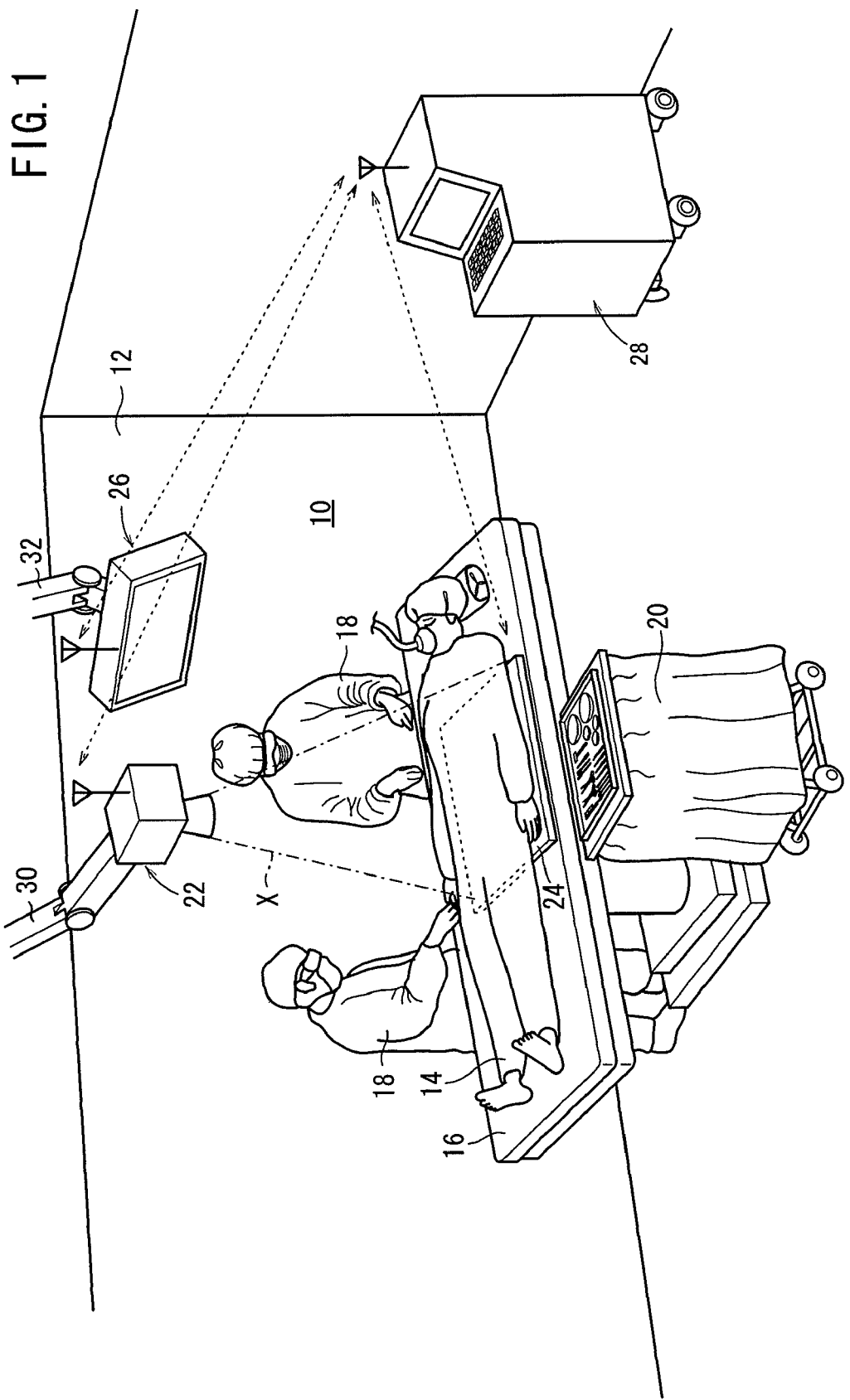
FIG. 1 is a perspective view of an operating room incorporating a radiation image capturing system according to an embodiment of the present invention.

FIG. 1 shows in perspective an operating room 12 incorporating a radiation image capturing system 10 according to an embodiment of the present invention. As shown in FIG. 1, the operating room 12 has, in addition to the radiation image capturing system 10, a surgical table 16 for a patient 14 to lie thereon, and an instrument table 20 disposed on one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus 22 for irradiating the patient 14 with a radiation X at a dose according to image capturing conditions, a radiation detecting cassette 24 housing therein a radiation detector, to be described later, for detecting the radiation X that has passed through the patient 14, a display device 26 for displaying a radiation image based on the radiation X that is detected by the radiation detector, and a console 28 for controlling the image capturing apparatus 22, the radiation detecting cassette 24, and the display device 26. The image capturing apparatus 22, the radiation detecting cassette 24, the display device 26, and the console 28 send and receive signals by way of wireless communications.

The image capturing apparatus 22 is coupled to a universal arm 30 so as to be movable to a desired position for capturing a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 2:
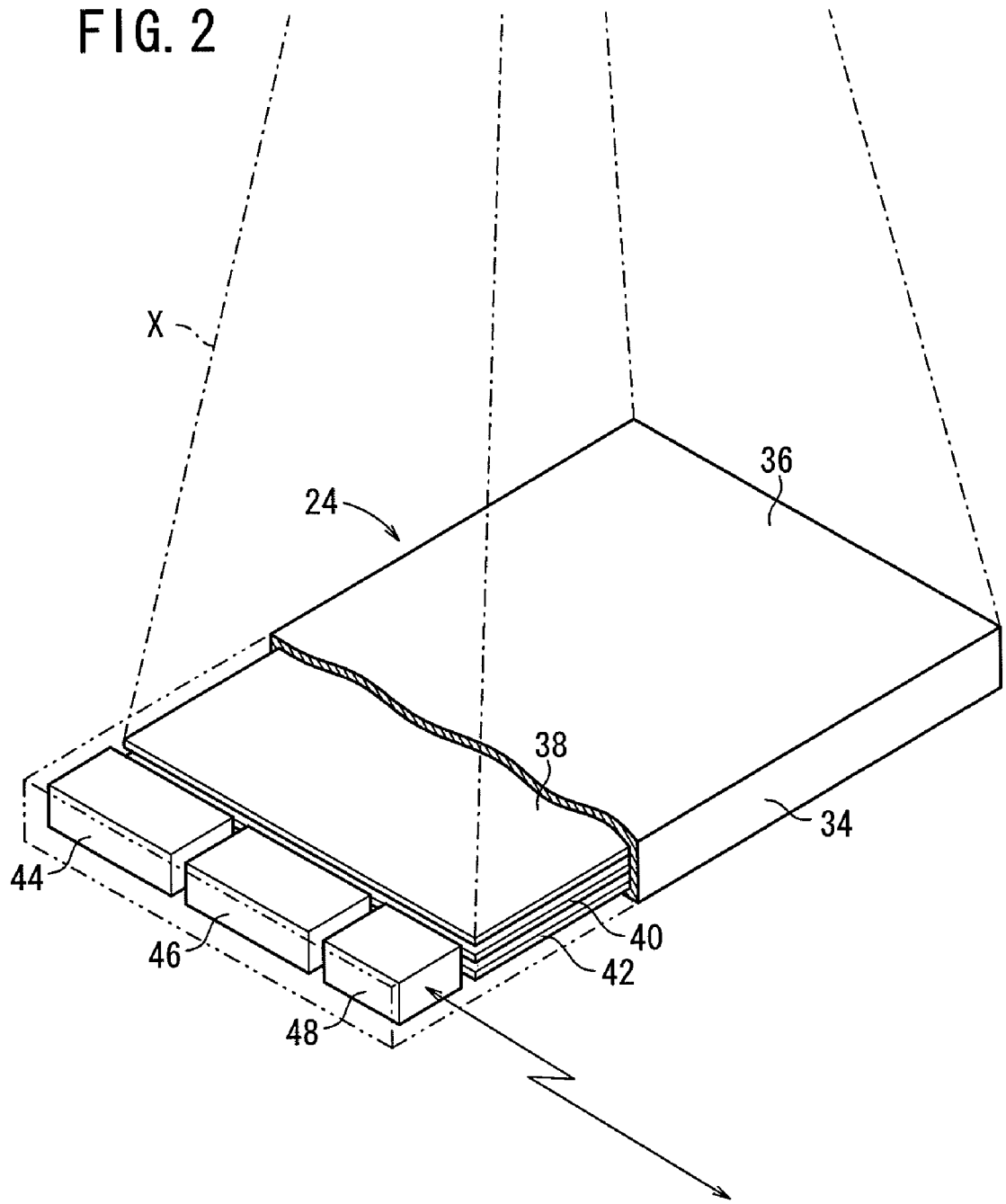
FIG. 2 is a perspective view, partly cut away, showing internal structural details of a radiation detecting cassette used in the radiation image capturing system.

FIG. 2 shows internal structural details of the radiation detecting cassette 24. As shown in FIG. 2, the radiation detecting cassette 24 has a casing 34 made of a material permeable to the radiation X. The casing 34 houses therein a grid 38 for removing scattered rays of the radiation X from the patient 14, a radiation detector (radiation conversion panel) 40 for detecting the radiation X that has passed through the patient 14, and a lead plate 42 for absorbing back scattered rays of the radiation X, which are successively arranged in the order named from a surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, a cassette controller 46 for energizing the radiation detector 40 with electric power supplied from the battery 44, and a transceiver 48 for sending and receiving signals including the information of the radiation X detected by the radiation detector 40, to and from the console 28. A shield plate of lead or the like should preferably be placed over the side surfaces of the cassette controller 46 and the transceiver 48 under the irradiated surface 36 of the casing 34 to protect the cassette controller 46 and the transceiver 48 against damage which would otherwise be caused if irradiated with the radiation X.

Figure 3:
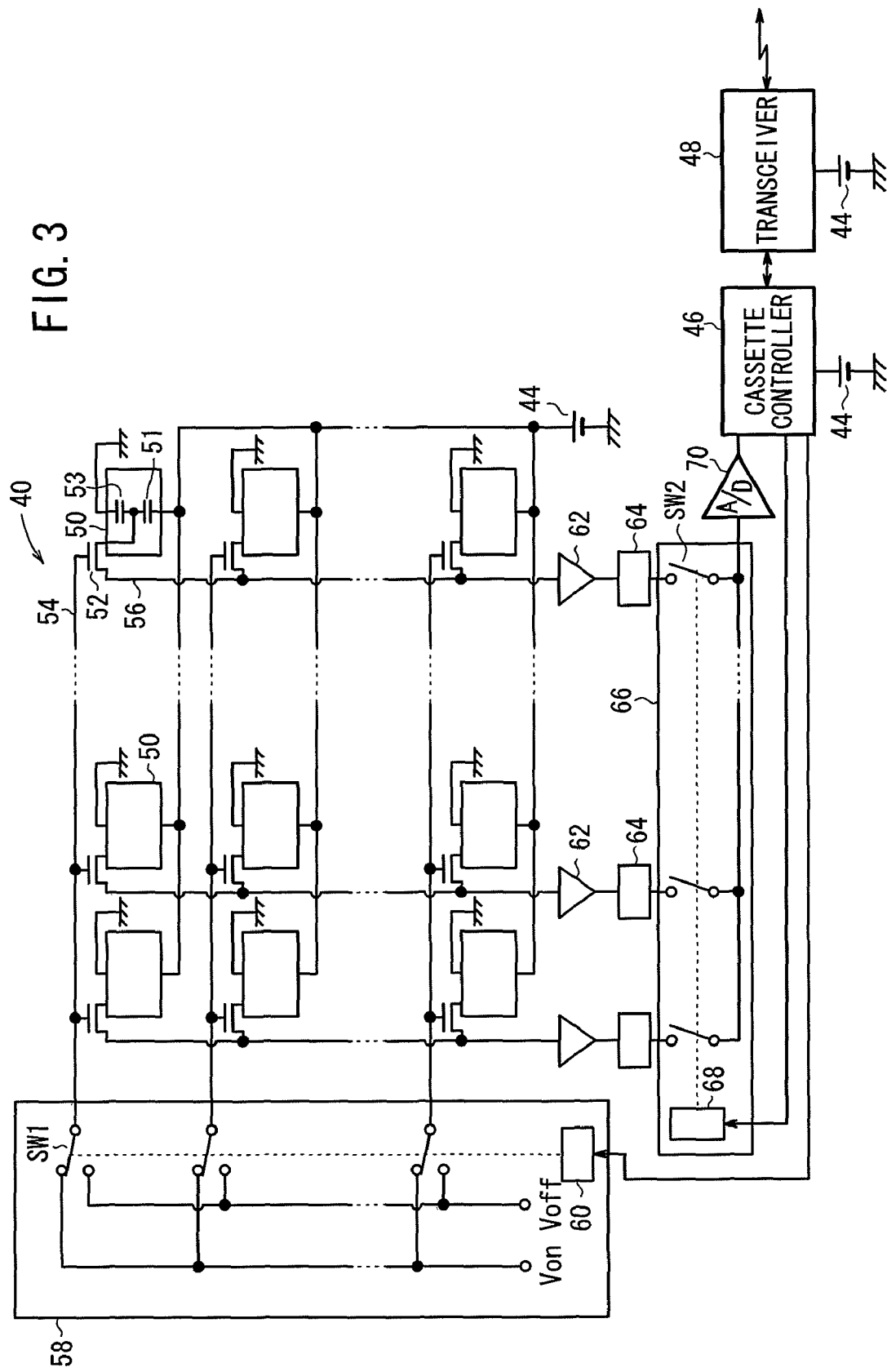
FIG. 3 is a block diagram of a circuit arrangement of a radiation detector of the radiation detecting cassette shown in FIG. 2.

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed on the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used in a certain temperature range. Therefore, some means for cooling the radiation detector 40 should preferably be provided in the radiation detecting cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 4:
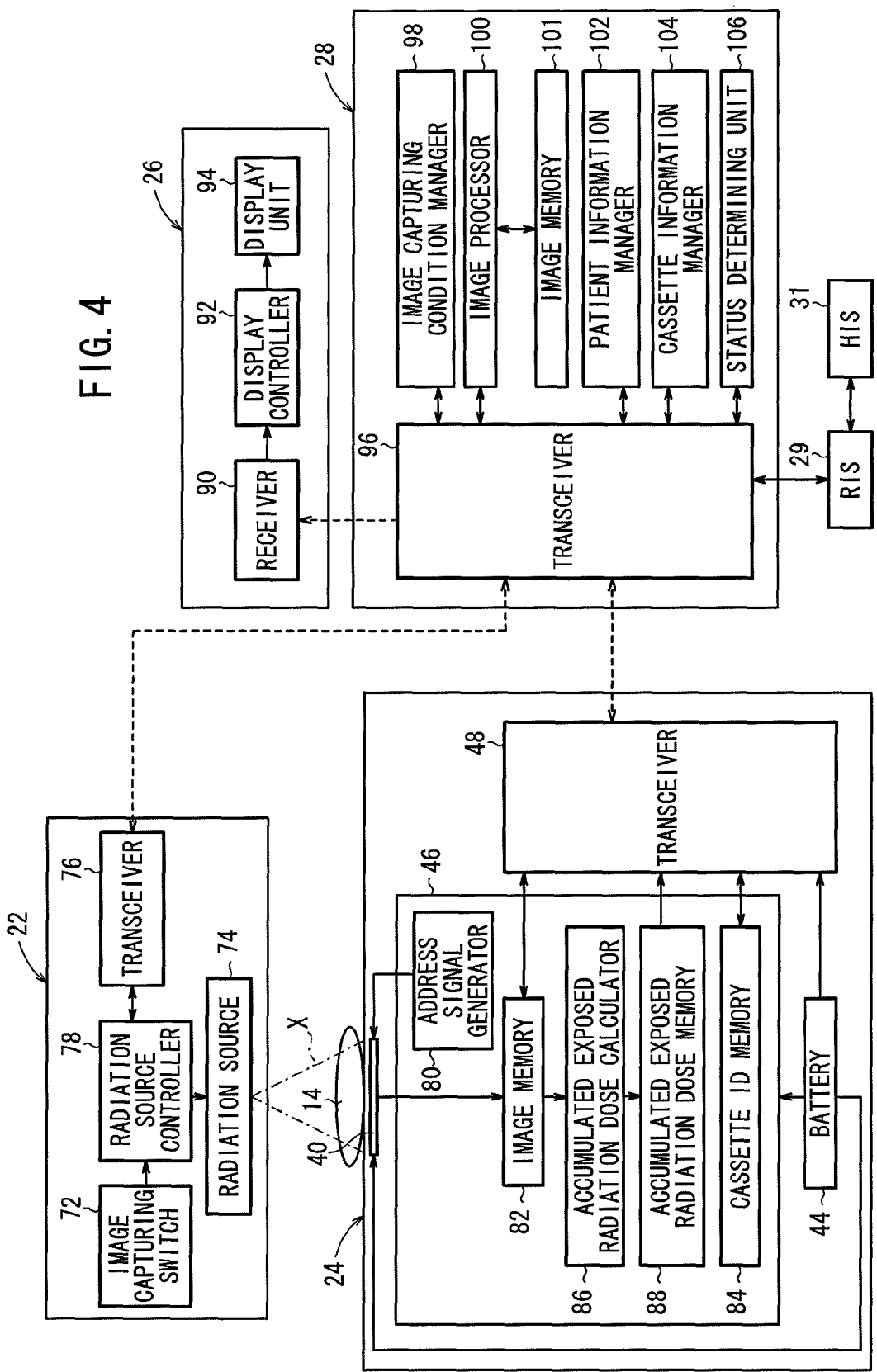
FIG. 4 is a block diagram of the radiation image capturing system.

FIG. 4 shows in block form the radiation image capturing system 10 which comprises the image capturing apparatus 22, the radiation detecting cassette 24, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 72, a radiation source 74 for outputting the radiation X, a transceiver 76 for receiving image capturing conditions from the console 28 by way of wireless communications and transmitting an image capturing completion signal, etc. to the console 28 by way of wireless communications, and a radiation source controller 78 for controlling the radiation source 74 based on an image capturing start signal supplied from the image capturing switch 72 and image capturing conditions supplied from the transceiver 76.

The radiation detecting cassette 24 houses therein the radiation detector 40, the battery 44, the cassette controller 46, and the transceiver (transmitting unit) 48. The cassette controller 46 comprises an address signal generator 80 for supplying address signals to the address decoder 60 of the line scanning driver 58 and the address decoder 68 of the multiplexer 66 of the radiation detector 40, an image memory 82 for storing the radiation image information detected by the radiation detector 40, a cassette ID memory 84 for storing cassette ID information for identifying the radiation detecting cassette 24, an accumulated exposed radiation dose calculator (accumulated exposed radiation dose calculating unit) 86 for calculating an accumulated exposed radiation dose applied to the radiation detecting cassette 24, and an accumulated exposed radiation dose memory 88 for storing the accumulated exposed radiation dose calculated by the accumulated exposed radiation dose calculator 86. The transceiver 48 receives a transmission request signal from the console 28 by way of wireless communications and transmits the cassette ID information stored in the cassette ID memory 84, the radiation image information stored in the image memory 82, and the accumulated exposed radiation dose stored in the accumulated exposed radiation dose memory 88 by way of wireless communications.

The display device 26 comprises a receiver 90 for receiving radiation image information from the console 28, a display controller 92 for controlling the display of the received radiation image information, and a display unit (warning unit) 94 for displaying the radiation image information processed by the display controller 92.

The console 28 comprises a transceiver 96 for transmitting and receiving necessary information including radiation image information to and from the image capturing apparatus 22, the radiation detecting cassette 24, and the display device 26 by way of wireless communications, an image capturing condition manager 98 for managing image capturing conditions required for the image capturing apparatus 22 to capture radiation images, an image processor (image processing unit) 100 for processing radiation image information transmitted from the radiation detecting cassette 24, an image memory 101 for storing the radiation image information processed by the image processor 100, a patient information manager 102 for managing patient information of the patient 14 whose images are to be captured, a cassette information manager (managing unit) 104 for managing cassette information including an accumulated exposed radiation dose transmitted from the radiation detecting cassette 24, and a status determining unit (determining unit) 106 for determining the status of the radiation detecting cassette 24 by comparing the accumulated exposed radiation dose with an allowable accumulated exposed radiation dose set in advance. The console 28 may be located outside of the operating room 12 insofar as it can transmit and receive signals to and from the image capturing apparatus 22, the radiation detecting cassette 24, and the display device 26 by way of wireless communications.

The image capturing conditions refer to condition for determining a tube voltage, a tube current, an irradiation time, etc. required to apply a radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for ordering the capture of an image, including the image capturing conditions and the patient information can be set directly on the console 28 or can be supplied from an external source to the console 28 via the RIS 29.

The cassette information refers to cassette ID information for identifying the radiation detecting cassette 24, and an accumulated exposed radiation dose applied to the radiation detecting cassette 24. The accumulated exposed radiation dose may represent, for example, a value produced by accumulating, at every image capturing, the maximum ones of the levels of the dose of the radiation X detected by the respective pixels 50 or of the radiation detector 40, or a value produced by accumulating, at every image capturing, the levels of the dose of the radiation X detected by certain pixels 50 of the radiation detector 40.

The radiation image capturing system 10 according to the present embodiment is basically constructed as described above, and operation of the radiation image capturing system 10 will be described below.

The radiation image capturing system 10 is installed in the operating room 12 and used when a radiation image of the patient 14 is required by the surgeons 18 who are performing an operation on the patient 14. Before a radiation image of the patient 14 is captured, patent information of the patient 14 to be imaged is registered in the patient information manager 102 of the console 28. If an area to be imaged of the patient 14 and an image capturing method have already been known, they are previously registered as image capturing conditions in the image capturing condition manager 98. After the above preparatory process is finished, the surgeons 18 perform an operation on the patient 14.

For capturing a radiation image of the patient 14 during the operation, one of the surgeons 18 or the radiological technician places the radiation detecting cassette 24 in a given position between the patient 14 and the surgical table 16 with the irradiated surface 36 facing the image capturing apparatus 22. Then, after having moved the image capturing apparatus 22 to a position confronting the radiation detecting cassette 24, one of the surgeons 18 or the radiological technician turns on the image capturing switch 72 to capture a radiation image of the patient 14.

The radiation source controller 78 of the image capturing apparatus 22 requests the console 28 to transmit the image capturing conditions from the image capturing condition manager 98 via the transceivers 96, 76. Based on the request, the console 28 transmits the image capturing conditions about the area to be imaged of the patient 14 to the image capturing apparatus 22 via the transceivers 96, 76 by way of wireless communication. When the radiation source controller 78 receives the image capturing conditions, it controls the radiation source 74 to apply a radiation X at a given dose to the patient 14 according to the image capturing conditions.

The radiation X which has passed through the patient 14 is applied to the grid 38, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges, which represent radiation image information of the patient 14, are read from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading radiation image information represented by the electric charges stored in the storage capacitors 53 of the pixels 50 connected to the selected gate line 54, through the signal lines 56.

The radiation image information (electric charges) read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges serving as radiation image information stored in the storage capacitors 53 of the pixels 50 connected to the successively selected gate lines 54 are read through the signal lines 56, and processed by the multiplexer 66 and the A/D converter 70 into digital signals, which are stored in the image memory 82 of the cassette controller 46.

The radiation image information transmitted from the image memory 82 through the transceiver 48 to the console 28 by way of wireless communication is received by the transceiver 96, processed by the image processor 100, and then stored in the image memory 101 in association with the patient information of the patient 14 registered in the patient information manager 102.

The radiation image information processed by the image processor 100 is transmitted from the transceiver 96 to the display device 26. In the display device 26, the receiver 90 receives the radiation image information, and the display controller 92 controls the display unit 94 to display a detailed radiation image based on the radiation image information. The surgeons 18 perform a surgical operation on the patient 14 while watching the radiation image displayed on the display unit 94.

Since no cables for transmitting and receiving signals are connected between the radiation detecting cassette 24 and the console 28, between the image capturing apparatus 22 and the console 28, and between the console 28 and the display device 26, no such cables are placed on the floor of the operating room 12 and hence there are no cable-induced obstacles to the operation performed by the surgeons 18, the radiological technician, or other staff members in the operating room 12.

The accumulated exposed radiation dose calculator 86 of the cassette controller 46 calculates an accumulated exposed radiation dose by accumulating the maximum ones of the levels of the dose of the radiation X representing the radiation image information detected by the respective pixels 50 of the radiation detector 40 and stored in the image memory 82, over a plurality of events in which radiation image information is captured by the radiation detecting cassette 24, and stores the accumulated exposed radiation dose in the accumulated exposed radiation dose memory 88.

Certain ones of the pixels 50 may be specified over which the patient 14 is less likely to be placed between the radiation source 74 and the radiation detecting cassette 24, and the accumulated exposed radiation dose calculator 86 may calculate an accumulated exposed radiation dose by accumulating the levels of the dose of the radiation X representing the radiation image information detected by those specified pixels 50. Alternatively, a dosage of the radiation X applied to the radiation detector 40 may be estimated based on the dosage of the radiation X output from the radiation source 74, and the accumulated exposed radiation dose calculator 86 may calculate an accumulated exposed radiation dose by accumulating estimated dosages.

The accumulated exposed radiation dose stored in the accumulated exposed radiation dose memory 88 is transmitted, together with the cassette ID information stored in the cassette ID memory 84 as identifying the radiation detecting cassette 24, to the console 28. Since the radiation detecting cassette 24 holds its own accumulated exposed radiation dose, the console 28 can supply information for determining the status of the radiation detecting cassette 24 even if the console 28 which receives the accumulated exposed radiation dose belongs to a different radiation image capturing system.

The cassette information manager 104 receives the information about the accumulated exposed radiation dose through the transceiver 96, and manages the received accumulated exposed radiation dose in association with the cassette ID information which identifies the radiation detecting cassette 24.

The status determining unit 106 compares the accumulated exposed radiation dose managed by the cassette information manager 104 with a predetermined allowable accumulated exposed radiation dose, and determines the status of the radiation detecting cassette 24. For example, if the accumulated exposed radiation dose exceeds the predetermined allowable accumulated exposed radiation dose after the present image capturing cycle, then the status determining unit 106 judges that a radiation image based on the captured radiation image information may possibly be low in quality because of a reduction in the sensitivity of the radiation detecting cassette 24, and issues a warning prompting the user to replace or service the radiation detecting cassette 24 on the console 28 and the display device 26 or to the RIS 29 and the HIS 31. By seeing the warning, the surgeons 18 or the radiological technician replaces or services the radiation detecting cassette 24 or makes a certain corrective action to make up for the reduction in the sensitivity of the radiation detecting cassette 24, thereby preventing an inappropriate radiation image from being captured.

Rather than comparing the accumulated exposed radiation dose after the present image capturing cycle with the allowable accumulated exposed radiation dose, the status determining unit 106 may compare the accumulated exposed radiation dose after the preceding image capturing cycle with the allowable accumulated exposed radiation dose before the image capturing apparatus 22 captures a radiation image, and determine whether the accumulated exposed radiation dose after the present image capturing cycle will exceed the allowable accumulated exposed radiation dose or not. If the status determining unit 106 judges that the accumulated exposed radiation dose after the present image capturing cycle will exceed the allowable accumulated exposed radiation dose, then the status determining unit 106 may prompt the user to replace or service the radiation detecting cassette 24 for thereby preventing, in advance, an inappropriate radiation image from being captured.

The accumulated exposed radiation dose may be stored, together with the cassette ID information for identifying the radiation detecting cassette 24, in the cassette information manager 104 of the console 28, instead of being stored in the accumulated exposed radiation dose memory 88 of the radiation detecting cassette 24. In this case, the cassette information manager 104 may read the cassette ID information from the cassette ID memory 84 of the radiation detecting cassette 24 that is being used to capture a radiation image, and retrieve the accumulated exposed radiation dose of the corresponding radiation detecting cassette 24 based on the cassette ID information, and the status determining unit 106 may compare the retrieved accumulated exposed radiation dose with the allowable accumulated exposed radiation dose to determine the status of the radiation detecting cassette 24.

In the radiation image capturing system 10 according to the illustrated embodiment, the radiation detector 40 housed in the radiation detecting cassette 24 directly converts the dose of the applied radiation X into an electric signal with the pixel 50. However, the radiation image capturing system 10 may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system 10 may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 5:
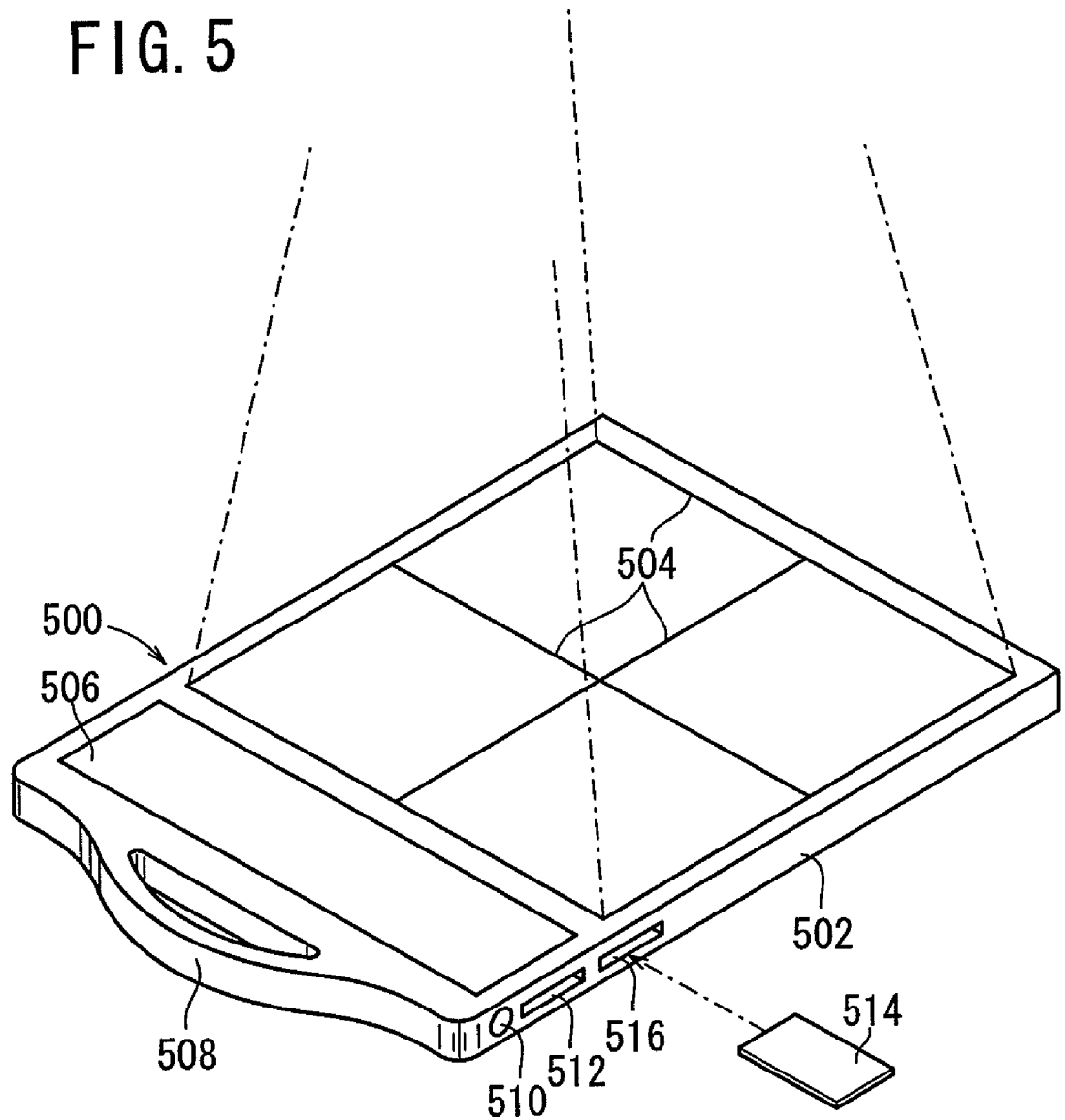
FIG. 5 is a perspective view showing a radiation detecting cassette in the radiation image capturing system according to another embodiment of the present invention.

Preferably, the radiation detecting cassette 500 may be constructed as shown in FIG. 5.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject can be positioned with respect to the radiation detecting cassette 500, and an area irradiated with the radiation can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a subject whose radiation image information is to be recorded on the radiation detecting cassette 500, the number of times the radiation detecting cassette 500 has been used, an accumulated exposed radiation dose, a charging state (remaining battery level) of a battery 44 in the radiation detecting cassette 500, image capturing conditions of radiation image information, and a positioning image of the subject with respect to the radiation detecting cassette 500. In this case, a technician confirms a subject based on the ID information displayed on the display section 506, for example, and also previously confirms that the radiation detecting cassette 500 is placed in a usable state. Then, the technician positions a desired captured area of the subject with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 44 in the radiation detecting cassette 500 becomes deteriorated, or when there is not enough time to fully charge the battery 44, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 6:
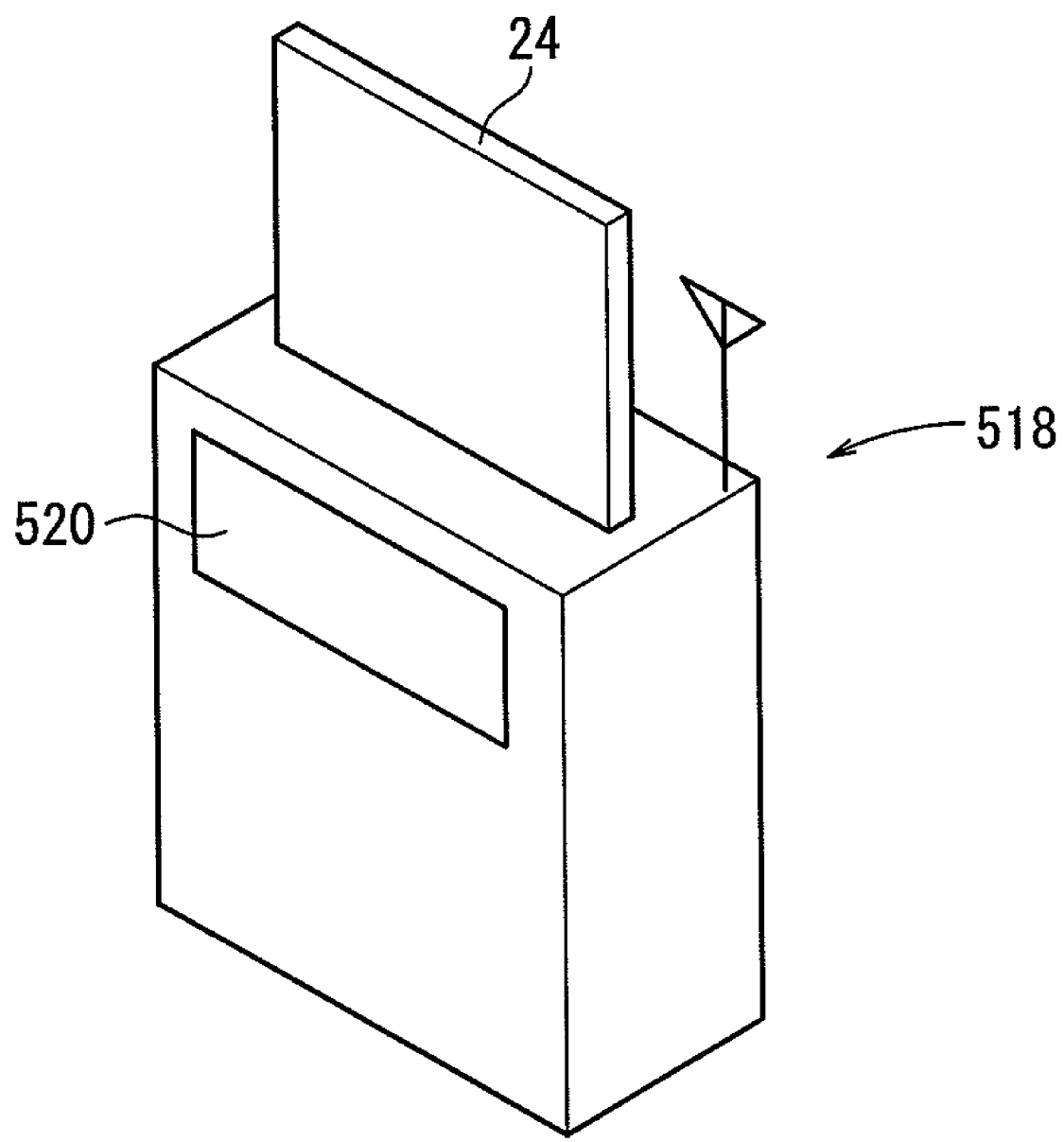
FIG. 6 is a perspective view showing a cradle which charges the radiation detecting cassette.

Preferably, a cradle 518 may be disposed in the operating room 12 or at a desired place in the hospital, into which the radiation detecting cassette 24 is inserted to charge the internal battery 44, as shown in FIG. 6. In this case, in addition to charging the battery 44, the cradle 518 may transmit and receive necessary information to and from external devices such as HIS 31, RIS 29, the console 28, etc. by way of wireless or wire communications of the cradle 518. The information may include radiation image information which is recorded on the radiation detecting cassette 24 inserted into the cradle 518.

Also, the cradle 518 may be provided with a display section 520. The display section 520 may display necessary information including a charging state of the inserted radiation detecting cassette 24 and radiation image information acquired from the radiation detecting cassette 24.

Further, a plurality of cradles 518 may be connected to a network. In this case, information about charging states of radiation detecting cassettes 24 inserted in respective cradles 518 can be collected through the network, and the radiation detecting cassette 24 in a usable state can be located.

Although a certain preferred embodiment of the present invention has been shown and described in detail, it should be understood that various changes and modifications may be made therein without departing from the scope of the appended claims.

What is claimed is:

1. A radiation image capturing system comprising:
   a radiation conversion panel for detecting a radiation that has passed through a subject and converting the detected radiation into radiation image information;
   an accumulated exposed radiation dose calculating unit for calculating an accumulated exposed radiation dose applied to said radiation conversion panel; and
   a determining unit for comparing the calculated accumulated exposed radiation dose with an allowable accumulated exposed radiation dose for said radiation conversion panel to determine a status of said radiation conversion panel;
   wherein said radiation conversion panel is housed in a radiation detecting cassette with a battery for energizing at least said radiation conversion panel;
   said accumulated exposed radiation dose calculating unit is disposed in said radiation detecting cassette;
   a transmitting unit is connected to said radiation conversion panel, for transmitting at least said accumulated exposed radiation dose to the outside of said radiation detecting cassette by way of wireless communications; and
   the accumulated exposed radiation dose calculation unit determines the exposed radiation cumulatively over multiple image capturing cycles.

2. A radiation image capturing system according to claim 1, wherein said transmitting unit transmits said radiation image information in addition to said accumulated exposed radiation dose.

3. A radiation image capturing system according to claim 1, wherein said accumulated exposed radiation dose calculating unit calculates said accumulated exposed radiation dose by accumulating the radiation image information detected by said radiation conversion panel, at every image capturing.

4. A radiation image capturing system according to claim 1, wherein said accumulated exposed radiation dose calculating unit estimates said accumulated exposed radiation dose by accumulating a dose of the radiation output from a radiation source, at every image capturing.

5. A radiation image capturing system according to claim 1, further comprising a managing unit for managing identification information for identifying said radiation conversion panel,
wherein said determining unit determines the status of said radiation conversion panel which is identified by said managing unit.

6. A radiation image capturing system according to claim 5, further comprising an identification information holding unit for holding said identification information, said identification information holding unit being connected to said radiation conversion panel,
wherein said managing unit identifies said radiation conversion panel according to the identification information acquired from said identification information holding unit.

7. A radiation image capturing system according to claim 1, further comprising a warning unit for issuing a warning with respect to the radiation conversion panel whose calculated accumulated exposed radiation dose is judged as exceeding said allowable accumulated exposed radiation dose by said determining unit.

8. A radiation image capturing system according to claim 7, wherein said warning unit comprises a display device disposed in a processing room in which an image of the subject is captured using said radiation conversion panel.

9. A radiation image capturing system according to claim 1, wherein said radiation conversion panel comprises a two-dimensional array of solid-state detecting devices for converting said radiation into electric charge information and holding the electric charge information.

10. A radiation image capturing system according to claim 1, wherein the accumulated exposed radiation dose calculation which is calculated by the accumulated exposed radiation dose calculating unit is not reset upon a start of each image capturing cycle.

* * * * *